United States Patent
Maeda

(10) Patent No.: US 10,591,450 B2
(45) Date of Patent: *Mar. 17, 2020

(54) LIQUID SAMPLE INTRODUCTION SYSTEM FOR ION SOURCE

(71) Applicant: SHIMADZU CORPORATION, Kyoto-shi, Kyoto (JP)

(72) Inventor: Kazuma Maeda, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/763,951

(22) PCT Filed: Sep. 29, 2015

(86) PCT No.: PCT/JP2015/077469
§ 371 (c)(1),
(2) Date: Aug. 20, 2018

(87) PCT Pub. No.: WO2017/056182
PCT Pub. Date: Apr. 6, 2017

(65) Prior Publication Data
US 2019/0011406 A1    Jan. 10, 2019

(51) Int. Cl.
*G01N 30/72* (2006.01)
*G01N 27/62* (2006.01)
(Continued)

(52) U.S. Cl.
CPC ......... *G01N 30/7266* (2013.01); *G01N 27/62* (2013.01); *H01J 49/045* (2013.01);
(Continued)

(58) Field of Classification Search
CPC .. G01N 30/7233; G01N 30/7266; G01N 1/02; G01N 2030/628; H01J 49/04;
(Continued)

(56) References Cited

U.S. PATENT DOCUMENTS

| | | |
|---|---|---|
| 5,703,360 A | 12/1997 | Fischer et al. |
| 6,207,954 B1 | 3/2001 | Andrien, Jr. et al. |

(Continued)

FOREIGN PATENT DOCUMENTS

| | | |
|---|---|---|
| JP | 200814788 A | 1/2008 |
| JP | 2009-031113 A | 2/2009 |

(Continued)

OTHER PUBLICATIONS

Written Opinion of the International Searching Authority of PCT/JP2015/077415 dated Dec. 8, 2015.

(Continued)

*Primary Examiner* — Brooke Purinton
(74) *Attorney, Agent, or Firm* — Sughrue Mion, PLLC

(57) ABSTRACT

A liquid sample introduction system for an ion source which ionizes a liquid sample by supplying the liquid sample to an ionization probe in an ion source and blowing an atomization-promoting gas at the liquid sample exiting from the tip of the ionization probe, the system including: a hermetically closable liquid sample container for holding a liquid sample; a liquid-supply-gas passage having one end connected to a point in a passage for an atomization-promoting gas leading to the ion source, and the other end connected to a space above a liquid level in the liquid sample container; a sample supply passage having one end connected to a space below the liquid level in the liquid sample container and the other end connected to the ionization probe; and a passage-switching unit in the sample supply passage for switching the sample supply passage between the communicating state and the closed state.

9 Claims, 3 Drawing Sheets

(51) Int. Cl.
 *H01J 49/04* (2006.01)
 *H01J 49/16* (2006.01)

(52) U.S. Cl.
 CPC ...... *H01J 49/0409* (2013.01); *H01J 49/0445* (2013.01); *H01J 49/165* (2013.01)

(58) Field of Classification Search
 CPC .. H01J 49/045; H01J 49/0404; H01J 49/0445; H01J 49/107
 See application file for complete search history.

(56) References Cited

U.S. PATENT DOCUMENTS

| | | | |
|---|---|---|---|
| 7,217,919 B2 | 5/2007 | Boyle et al. | |
| 2008/0237458 A1 | 10/2008 | Wang | |
| 2009/0242749 A1 | 10/2009 | Bajic | |
| 2009/0314057 A1* | 12/2009 | Hatscher | B01D 59/44 73/23.35 |
| 2010/0096542 A1 | 4/2010 | Whitehouse et al. | |
| 2013/0146479 A1* | 6/2013 | Brouwer | G01N 24/08 205/780.5 |
| 2014/0284473 A1* | 9/2014 | Ueda | H01J 49/0445 250/288 |
| 2014/0373605 A1* | 12/2014 | Nichols | G01N 30/20 73/61.55 |
| 2015/0102232 A1 | 4/2015 | Satake et al. | |

FOREIGN PATENT DOCUMENTS

| | | |
|---|---|---|
| JP | 5740525 B2 | 6/2015 |
| WO | 2013/132676 A1 | 9/2013 |

OTHER PUBLICATIONS

International Search Report of PCT/JP2015/077415 dated Dec. 8, 2015.
Written Opinion of PCT/JP2015/077469 dated Dec. 8, 2015 [PCT/ISA/237].
International Search Report of PCT/JP2015/077469 dated Dec. 8, 2015 [PCT/ISA/210].
Extended European Search Report dated Jul. 19, 2019 issued by the European Patent Office in counterpart application No. 15905337.0.
Non Final Office Action dated May 10, 2019, for corresponding U.S. Appl. No. 15/764,129.

* cited by examiner

Fig. 3

| Measurement Time | Sample Name | Component Name | Retention Time | Mass Range to Be Measured | Liquid Sample Container (Reference Lquid Sample) | Valve Position |
|---|---|---|---|---|---|---|
| 0.0-10.0min. | Sample 1 | Component A | 3.0-4.0min. | 10-500 | 70a | a |
| | | Component B | 5.0-6.0min. | 300-2000 | 70b | b |
| | | Component C | 8.0-9.5min. | 500-3000 | 70d | d |
| 10.0-20.0min. | Sample 2 | Component D | 3.0-4.0min. | 10-500 | Not used | f |
| | | Component E | 5.0-6.0min. | 300-2000 | Not used | f |
| | | Component F | 8.0-9.5min. | 500-3000 | Not used | f |
| 20.0-30.0min. | Sample 3 | Component A | 3.0-4.0min. | 10-500 | 70a | a |
| | | Component B | 5.0-6.0min. | 300-2000 | 70b | b |
| | | Component C | 8.0-9.5min. | 500-3000 | 70d | d |

Fig. 4

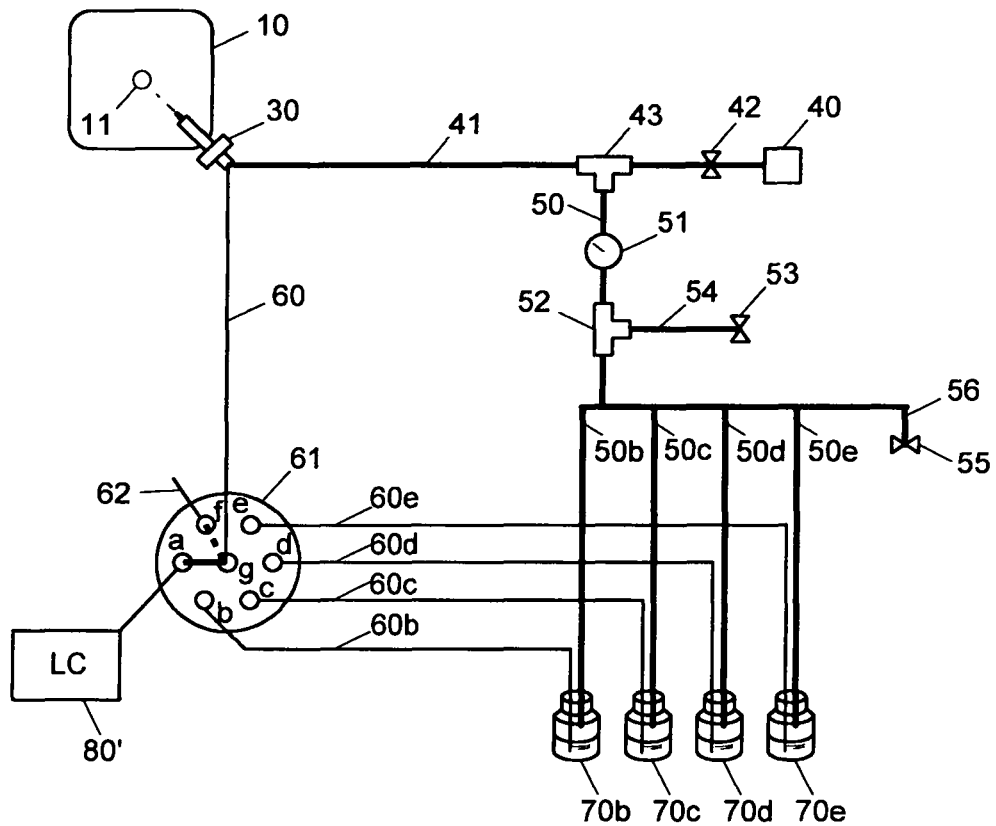

LIQUID SAMPLE INTRODUCTION SYSTEM FOR ION SOURCE

CROSS REFERENCE TO RELATED APPLICATIONS

This application is a National Stage of International Application No. PCT/JP2015/077469, filed Sep. 29, 2015.

TECHNICAL FIELD

The present invention relates to a liquid sample introduction system for an ion source used for introducing a liquid sample into an ion source in an ion analyzer, such as a mass spectrometer.

BACKGROUND ART

A mass spectrometer is one type of device for analyzing components contained in a liquid sample. A mass spectrometer includes an ion source for ionizing components in a liquid sample and a mass spectrometry section for separating and detecting the ionized components according to their mass-to-charge ratios. In an ion source for ionizing a liquid sample (e.g. ESI source or APCI source), the ionization of a liquid sample is normally achieved by supplying the liquid sample to an ionization probe and making an atomization-promoting gas (which may also be called a "nebulizer gas" or "drying gas") blow at the liquid sample exiting from the tip of the ionization probe.

For example, a liquid sample introduction system described in Patent Literature 1 is used to introduce a liquid sample into the previously described type of ion source. In this liquid sample introduction system, a liquid-supply gas is sent into the space above the liquid surface in a hermetically closable container holding a liquid sample (liquid sample container) to supply the liquid sample from the liquid sample container to the ionization probe of the ion source by the pressure of the liquid-supply gas.

CITATION LIST

Patent Literature

Patent Literature 1: U.S. Pat. No. 5,703,360 B

SUMMARY OF INVENTION

Technical Problem

The previously described liquid sample introduction system requires the liquid-supply gas for sending a liquid sample in addition to the atomization-promoting gas which is made to blow at the liquid sample in the ion source. The necessity of preparing gas sources for the two kinds of gas inevitably increases the cost of the device.

Although the description thus far has been concerned with a mass spectrometer, a similar problem occurs in an ion mobility spectrometer or other types of devices in which ions are generated from a liquid sample and subjected to an analysis.

The problem to be solved by the present invention is to provide a liquid sample introduction system for an ion source with which liquid samples can be ionized at a low cost.

Solution to Problem

In order to solve the aforementioned problem, the applicant proposes, in an international patent application (PCT/JP2015/077415) which is filed on the same date as the present application, a liquid sample introduction system for an ion source which ionizes a liquid sample by supplying the liquid sample to an ionization probe in an ion source and making an atomization-promoting gas blow at the liquid sample exiting from the tip of the ionization probe, the liquid sample introduction system including:

a liquid sample container which is a hermetically closable container for holding a liquid sample;

a liquid-supply-gas passage having one end connected to a point in a passage for an atomization-promoting gas leading to the ion source, and the other end connected to a space above a liquid level in the liquid sample container; and a sample supply passage having one end connected to a space below the liquid level in the liquid sample container and the other end connected to the ionization probe.

In the aforementioned liquid sample introduction system for an ion source, the liquid-supply-gas passage is connected to a point in the passage for an atomization-promoting gas leading to the ion source. A portion of the atomization-promoting gas is thereby introduced into the liquid sample container, and the liquid sample is sent from the liquid sample container to the ionization probe of the ion source by the pressure of the atomization-promoting gas. In other words, the atomization-promoting gas intended for use in the ion source is additionally used as the liquid-supply gas. Accordingly, it is unnecessary to add a supply source of the liquid-supply gas for sending the liquid sample to the ion source, and the ionization of the liquid sample can be achieved at a low cost.

Discontinuing the supply of the atomization-promoting gas to the ion source in an ion analyzer causes a decrease in the pressure in the ionization chamber to which the atomization-promoting gas is supplied as well as a change in the flow of gas within the ionization chamber. This causes a change in the ion ionization efficiency for the liquid sample as well as a change in the efficiency of the introduction of the generated ions into an analysis chamber located behind the ionization chamber. To avoid such a situation, it is common for an ion analyzer to continuously supply a constant amount of atomization-promoting gas even when the device is being prepared for or is standing by for an analysis (i.e. when no liquid sample is supplied).

In the case of the aforementioned liquid sample introduction system for an ion source, when the nebulizer gas is supplied to the ion source, the atomization-promoting gas is also simultaneously supplied to the liquid sample container as the liquid-supply gas. This causes a new problem that the liquid sample is continuously supplied to the ionization probe and is needlessly consumed.

The present invention developed for solving the previously described problem is a liquid sample introduction system for an ion source which ionizes a liquid sample by supplying the liquid sample to an ionization probe in an ion source and making an atomization-promoting gas blow at the liquid sample exiting from the tip of the ionization probe, the liquid sample introduction system including:

a) a liquid sample container which is a hermetically closable container for holding a liquid sample;

b) a liquid-supply-gas passage having one end connected to a point in a passage for an atomization-promoting gas leading to the ion source, and the other end connected to a space above a liquid level in the liquid sample container;

c) a sample supply passage having one end connected to a space below the liquid level in the liquid sample container and the other end connected to the ionization probe; and d) a passage-switching unit, located in the sample supply passage, for switching the sample supply passage between the communicating state and the closed state.

The liquid sample introduction system for an ion source according to the present invention is a modified version of the liquid sample introduction system for an ion source proposed in the aforementioned international patent application, in which a passage-switching unit is additionally placed in the sample supply passage to make the sample supply passage switchable between the communicating state and the closed state. The liquid sample introduction system for an ion source according to the present invention, can be switched between the connecting state for supplying the liquid sample to the ionization probe and the closed state for discontinuing the supply of the liquid sample. Accordingly, the liquid sample will not be needlessly consumed even when the atomization-promoting gas is continuously supplied to the ion source.

For the ionization of a liquid sample, a drying gas may additionally be used with the atomization-promoting gas. Such an ion source might allow the drying gas to be used for the supply of the liquid sample. However, this idea is only applicable in an ion source which uses a drying gas. The liquid sample introduction system for an ion source according to the present invention utilizes the atomization-promoting gas, which is commonly used for ionizing a liquid sample by atmospheric pressure ionization regardless of the kind of liquid sample. Therefore, the present system can be used for various kinds of liquid samples and various types of ion sources.

The liquid sample introduction system for an ion source according to the present invention may preferably include a liquid-supply-gas pressure regulator for regulating the pressure of the gas flowing through the liquid-supply-gas passage.

In the aforementioned mode of the liquid sample introduction system for an ion source including the liquid-supply-gas pressure regulator, the pressure of the liquid-supply gas can be regulated independently of the pressure of the atomization-promoting gas supplied to the ion source, so as to change the amount of liquid sample to be supplied to the ion source.

Furthermore, the liquid sample introduction system for an ion source according to the present invention may be configured as follows:

a plurality of the liquid sample containers are provided;

the other end of the liquid-supply-gas passage is branched into a plurality of liquid-supply-gas sub-passages each of which is connected to the space above the liquid level in one of the liquid sample containers;

the one end of the sample-supply passage is branched into a plurality of sample-supply sub-passages each of which is connected to the space below the liquid level in one of the liquid sample containers; and the passage-switching unit is a passage-switching valve placed at the branching point of the sample-supply sub-passages, the passage-switching valve having one main port and a plurality of sub-ports to be selectively connected to the main port, where one of the plurality of sub-ports is open to atmospheric pressure, and the plurality of sample-supply sub-passages are connected to the other sub-ports.

This mode of the liquid sample introduction system for an ion source uses a single passage-switching valve to selectively introduce a plurality of liquid samples into the ion source.

Advantageous Effects of the Invention

With the liquid sample introduction system for an ion source according to the present invention, a liquid sample can be introduced into and ionized by an ion source at a low cost. The liquid sample will not be needlessly consumed even when the atomization-promoting gas is continuously supplied to the ion source.

BRIEF DESCRIPTION OF DRAWINGS

FIG. 3 is one example of the analysis conditions to be set in the present embodiment.

FIG. 4 is another configuration example of the liquid sample introduction system for an ion source according to the present invention.

DESCRIPTION OF EMBODIMENTS

Figure 1:
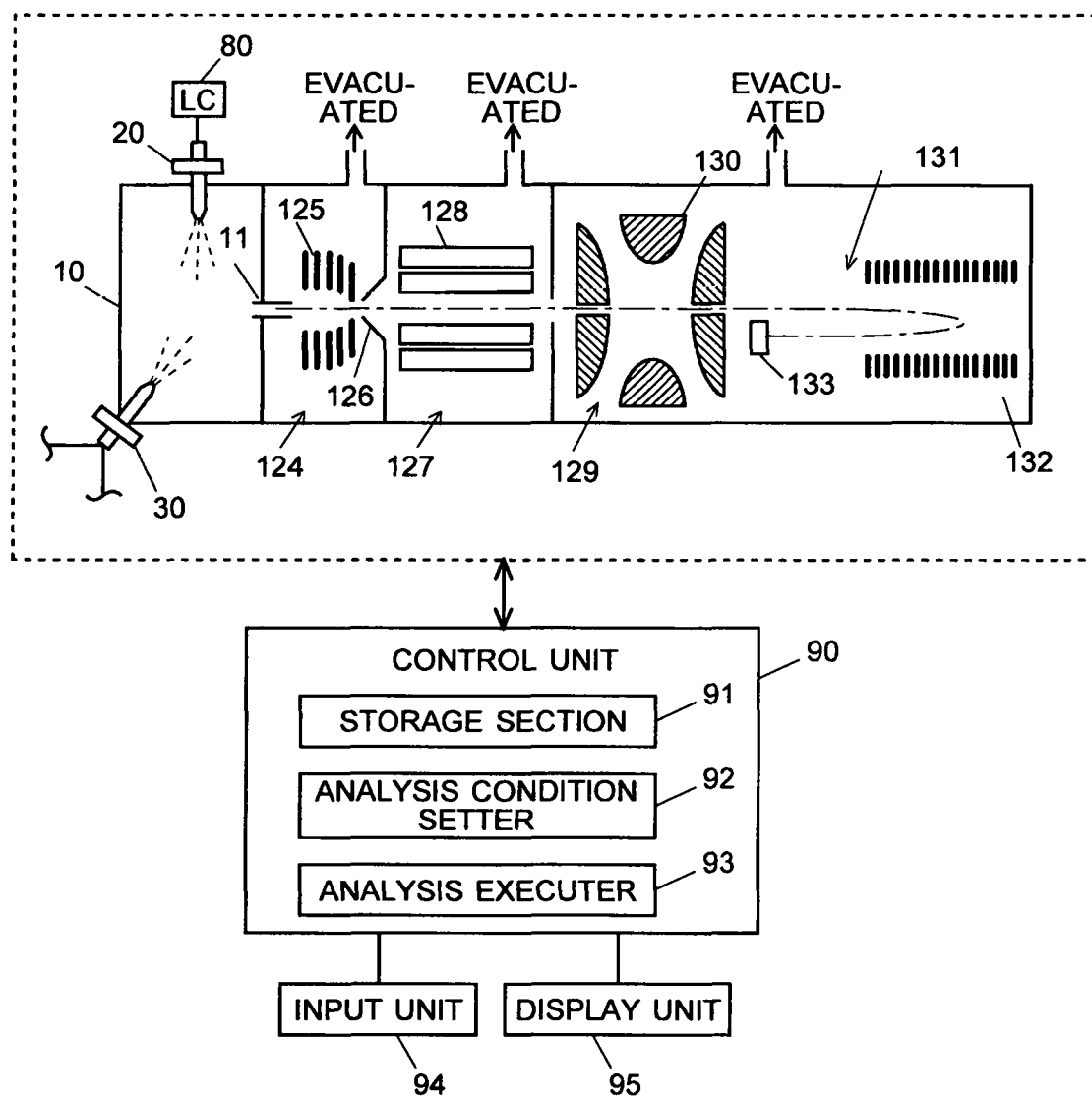
FIG. 1 is a configuration diagram showing the main components of a mass spectrometer including a liquid sample introduction system for an ion source according to the present invention.

An embodiment of the liquid sample introduction system for an ion source according to the present invention is hereinafter described with reference to the drawings. The liquid sample introduction system for an ion source according to the present embodiment is used for introducing a reference liquid sample for mass calibration into a time-of-flight mass spectrometer (which may hereinafter be called the "TOF-MS") in a mass spectrometric analysis for various components in a liquid sample to be analyzed (which is hereinafter called the "target liquid sample") which is eluted from a liquid chromatograph 80. Although a TOF-MS is used as the ion analyzer in the present embodiment, a liquid sample introduction system for an ion source having a similar configuration to the present embodiment can also be used in other types of mass spectrometers or ion analyzers (e.g. ion mobility spectrometers).

Each section of the liquid chromatograph 80, liquid sample introduction system for an ion source, and TOF-MS is controlled by a control unit 90. The control unit 90 includes a storage section 91 as well as an analysis condition setter 92 and an analysis executer 93 as its functional blocks. The control unit 90 is actually a computer on which the required software has been installed. An input unit 94 and a display unit 95 are connected to the control unit 90. The analysis condition setter 92 sets analysis conditions based on an input by a user, prepares an analysis execution file, and saves it to the storage section 91. Upon receiving a command issued by the user, the analysis executer 93 conducts an analysis for various components in the target liquid sample by operating each section of the liquid chromatograph 80, liquid sample introduction system for an ion source, and TOF-MS based on the analysis execution file.

The TOF-MS includes an ionization chamber 10 maintained at atmospheric pressure and an analysis chamber 129 maintained in a high vacuum state by being evacuated with a vacuum pump (not shown). First and second intermediate vacuum chambers 124 and 127 having their degrees of vacuum increased in a stepwise manner are located between the ionization chamber 10 and the analysis chamber 129. The ionization chamber 10 communicates with the first intermediate vacuum chamber 124 through a thin desolvation tube 11. The first intermediate vacuum chamber 124 communicates with the second intermediate vacuum chamber 127 through a small orifice bored at the apex of a conical skimmer 126.

The various components in a target liquid sample which have been temporally separated by the column of the liquid chromatograph 80 are turned into electrically charged droplets by an ESI probe 20 and sprayed into the ionization chamber 10. Similarly, a reference liquid sample for mass calibration supplied from a liquid sample introduction system for an ion source (which will be described later) is also transformed into electrically charged droplets by an ESI probe 30 and sprayed into the ionization chamber 10. Those charged droplets collide with gas molecules within the ionization chamber 10, being broken into even finer droplets, which are quickly dried (desolvated) and turned into ions. Due to the pressure difference between the ionization chamber 10 and the first intermediate vacuum chamber 124, those ions are drawn into the desolvation tube 11. Being converged by ion guides 125 and 128, the ions travel through the two intermediate vacuum chambers 124 and 127, to be introduced into a three-dimensional quadrupole ion trap 130 inside the analysis chamber 129.

In the ion trap 130, the ions are temporarily captured by and stored in a quadrupole electric field created by radio-frequency voltages applied from a power source (not shown) to the electrodes. The various ions stored within the ion trap 130 are simultaneously given a specific amount of kinetic energy and thereby ejected from the ion trap 130 into a time-of-flight mass separator (TOF) 131. The TOF 131 includes reflectron electrodes 132, to which DC voltages are respectively applied from a DC power source (not shown). Due to the effect of the DC electric field created by those electrodes, the ions are returned and reach an ion detector 133. Among the ions which have been simultaneously ejected from the ion trap 130, an ion having a smaller mass-to-charge ratio flies at a higher speed. Accordingly, the ions arrive at the ion detector 133 showing time differences depending on their mass-to-charge ratios. The ion detector 133 generates, as a detection signal, an electric current corresponding to the number of ions which have arrived at the detector. The output signals from the ion detector 133 are saved in the storage section 91 of the control unit 90 (which will be described later).

As just described, the liquid sample introduction system for an ion source according to the present embodiment is a system for introducing a reference liquid sample for mass calibration into the ionization chamber 10 of the TOF-MS to ionize the reference liquid sample along with the liquid sample eluted from the column of the liquid chromatograph 80. Each of the five reference liquid samples a-e contains components which produce ions having mass to charge ratios different from one another and is contained in liquid sample containers 70a-70e respectively.

A nebulizer gas passage 41 extending from a nitrogen gas cylinder (atomization gas source) 40 is connected to the ESI probe 30 provided in the ionization chamber 10. In the nebulizer gas passage 41, a valve 42 and a branching unit 43 are provided in the mentioned order from the nitrogen gas cylinder 40. A liquid-supply-gas passage 50 is connected to the branching unit 43. The liquid-supply-gas passage 50 is provided with a regulator 51 and a branching unit 52. A relief passage 54 leading to a relief valve 53 is connected to the branching unit 52.

The liquid-supply-gas passage 50 is branched into five liquid-supply-gas sub-passages 50a-50e. The ends of the liquid-supply-gas sub-passages 50a-50e are respectively lead to the spaces above the liquid levels in the containers (liquid sample containers) 70a-70e each of which contains a reference liquid sample. An atmospheric open passage 56 leading to an atmospheric open valve 55 is provided parallel to the liquid-supply-gas sub-passages 50a-50e.

Additionally, a sample supply passage 60 is connected to the ESI probe 30. The other end of the sample supply passage 60 is connected to the main port 61g of a six-position seven-way valve 61. The six-position seven-way valve 61 has six sub-ports 61a-61f. One of the sub-ports 61a-61f can be connected to the main port 61g. One end of each of the sample-supply sub-passages 60a-60e is connected to each of the sub-ports 61a-61e. The other ends of the sample-supply sub-passages 60a-60e are respectively lead to the spaces below the liquid levels (i.e. submerged in the liquid) in the liquid sample containers 70a-70e. One end of an atmospheric open passage 62 is connected to the sub-port 61f. The other end of the atmospheric open passage 62 is open to the atmosphere.

An analysis operation in the present embodiment is hereinafter described.

A user enters analysis parameters for each of the one or more components which may possibly be contained in a target liquid sample, the parameters including: the name of the component; the time segment during which the component will be eluted from the column of the liquid chromatograph 80 (retention time); the mass range to be measured in a mass spectrometric analysis of the component in the TOF-MS; and the kind of reference liquid sample for mass calibration to be used as an internal reference in the mass spectrometric analysis of the component (or the identification number of the liquid sample container in which the reference liquid sample concerned is contained). Based on those parameters, the analysis condition setter 92 in the control unit 90 prepares an analysis condition file and saves it to the storage section 91. As for the reference liquid sample to be used in the mass spectrometric analysis of each component, a liquid sample should be selected which generates a plurality of kinds of ions which satisfy the condition that their mass-to-charge ratios are included within the mass range to be measured for the component and yet do not overlap the mass-to-charge ratios of the ions to be generated from the same component. In the present embodiment, as shown in FIG. 3, an analysis condition file for a batch analysis of three target liquid samples 1-3 are prepared. For the target liquid samples 1 and 3, a mass spectrometric analysis using a reference liquid sample for the component in the target liquid sample is performed. As for the target liquid sample 2, the mass spectrometric analysis is performed without using a reference liquid sample.

The present description deals with the case where the user enters the retention time, mass range to be measured, and kind of reference liquid sample for each component. As another possible case, component analysis information in which the information concerning the retention time, mass range to be measured and kind of reference liquid sample is related to each of the components may be stored in the storage section 91. In this case, upon receiving to an input of the name of a component by a user, the analysis condition setter 92 can refer to the component analysis information stored in the storage section 91 to automatically determine the retention time, mass range to be measured, and kind of reference liquid sample, and prepare an analysis condition file.

When a command to initiate an analysis is issued by the user, the analysis executer 93 introduces a target liquid sample into the liquid chromatograph 80. The target liquid sample is carried into the column by the flow of a mobile phase. After being temporally separated from each other within the column of the liquid chromatograph 80, the various components in the target liquid sample 1-3 are sequentially introduced into and ionized by the ESI probe 20, to be subjected to mass spectrometry.

Concurrently with the analysis operation, the liquid sample introduction system for an ion source sequentially supplies liquid samples to the ESI probe 30 as follows, based on the previously mentioned analysis conditions: The liquid sample in the liquid sample container 70a is initially supplied from the beginning of the series of measurements (from the beginning of the measurement for target liquid sample 1) until the elapse of 4.5 minutes (until the middle point of the period of time between the ending time of the analysis of component A and the beginning time of the analysis of component B). Subsequently, the liquid sample in the liquid sample container 70b is supplied until the elapse of 7.0 minutes (until the middle point of the period of time between the ending time of the analysis of component B and the beginning time of the analysis of component C). After that, the reference liquid sample in the liquid sample container 70d is supplied until the completion of the analysis.

When the measurement time has reached 10 minutes, the measurement for liquid sample 2 is initiated. No reference liquid sample is supplied during the measurement for liquid sample 2 (measurement time: 10-20 minutes). When the measurement time has reached 20 minutes, the measurement for liquid sample 3 is initiated, in which the reference liquid samples 70a, 70b and 70d which respectively correspond to components A, B and C are sequentially supplied, as in the mass spectrometric analysis of liquid sample 1.

During the previously described series of measurements, each section of the liquid sample introduction system for an ion source operates as follows:

Nitrogen gas is supplied from the nitrogen gas cylinder 40 into the nebulizer gas passage 41 at a flow rate of 3 L/min and with a pressure of +500 kPa, where L is the length of the passage from the ESI probe 30 to the valve 42. The notation of "+500 kPa" means that the pressure concerned is higher than the pressure in the ionization chamber 10 by 500 kPa. For example, if the ionization chamber 10 is at atmospheric pressure (101.325 kPa), the nitrogen gas is supplied with a pressure of 601.325 kPa. It should be noted that the numerical values of the flow rate and pressure of the nitrogen gas supplied into the nebulizer gas passage 41 as well as the pressure of the liquid-supply gas are mere examples. The user may appropriately change those values. The flow rate and pressure of the nebulizer gas can be determined according to the specifications of the used ionization probe (in the present embodiment, ESI probe 30) and other relevant factors. The pressure of the liquid-supply gas can be determined according to the desired amount of reference liquid sample to be supplied. It should be noted that both the pressure of the nebulizer gas and that of the liquid-supply gas should be higher than the pressure within the ionization chamber 10.

The nitrogen gas flowing from the branching unit 43 into the liquid-supply-gas passage 50 is sent through the liquid-supply-gas sub-passages 50a-50e to the liquid sample containers 70a-70e after its pressure is reduced to +100 kPa by the regulator 51. Thus, the pressures in all liquid sample containers 70a-70e are simultaneously increased, whereby the reference liquid samples respectively contained in the liquid sample containers 70a-70e are pushed into the sample-supply sub-passages 60a-60e, respectively. If the gas pressure in the liquid-supply-gas passage 50 has increased to a level of +150 kPa or higher due to a problem with the regulator 51, the relief valve 53 is opened to release the nitrogen gas.

Figure 2:
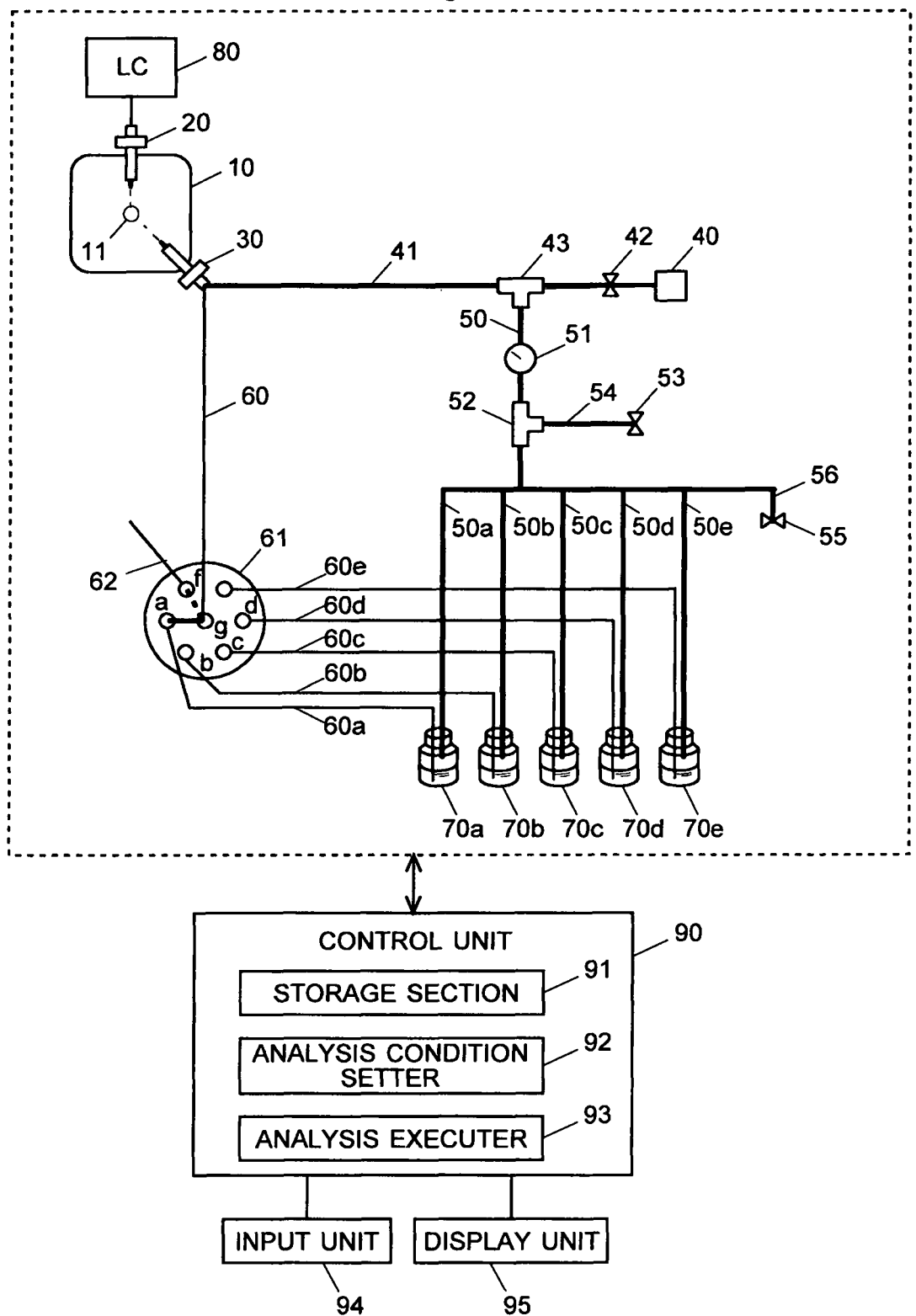
FIG. 2 is a configuration example of the liquid sample introduction system for an ion source according to the present invention.

The reference liquid samples pushed into the sample-supply-gas sub-passages 60a-60e respectively reach the sub-ports 61a-61e of the six-position seven-way valve 61. In the six-position seven-way valve 61, only one of the sub-ports 61a-61e is connected to the main port 61g. At the beginning of the series of measurements (i.e. at the beginning of the measurement for target liquid sample 1), the reference liquid sample sent to the sub-port 61a (i.e. the reference liquid sample contained in the liquid sample container 70a) flows through the main port 61g into the sample supply passage 60 (see the solid line in FIG. 2), to be introduced into the ESI probe 30. After that, the passage in the six-position seven-way valve 61 is switched with the elapse of the analysis time so that reference liquid samples b and d are sequentially and individually supplied to the ESI probe 30. During the measurement for target liquid sample 2, the sub-port 61f of the six-position seven-way valve 61 is connected to the main port 61g (see the dashed line in FIG. 2). The sub-port 61f has the atmospheric open passage 62 connected. Therefore, the atmospheric open passage 62, sub-port f, main port g, and sample supply passage 60 are all made to be open to the atmosphere, and the supply of the liquid sample is discontinued. Meanwhile, the supply of the nebulizer gas to the ESI probe 30 is continued. At a later point in time when the measurement for target liquid sample 3 is initiated, the sub-port 61a is connected to the main port 61g to supply the reference liquid sample in the liquid sample container 70a to the ESI probe 30.

At the completion of the entire series of measurements, the sub-port 61d of the six-position seven-way valve 61 is connected to the main port 61g, and the reference liquid sample in the liquid sample container 70d is being supplied to the ESI probe 30. In the present embodiment, if any one of the reference liquid samples is being supplied to the ESI probe 30 at the completion of a batch analysis (i.e. if any one of the sub-ports 61a-61e is connected to the main port 61g), the analysis executer 93 operates the six-position seven-way valve 61 to connect the sub-port 61f to the main port 61g after the elapse of a predetermined length of time (e.g. five minutes). It is naturally possible for the user to manually switch the passage in the previously described manner after the completion of the batch analysis. The supply of the liquid sample is thereby discontinued. Subsequently, the atmospheric open valve 55 is opened to restore the liquid sample containers 70a-70e to ordinary pressure and allow the user to perform necessary tasks, such as replacing the liquid sample containers 70a-70e with new ones.

In the present embodiment, after a predetermined length of time has passed since the completion of the batch analysis, the analysis executer 93 automatically switches the passage in the six-position seven-way valve 61 to discontinue the supply of the reference liquid samples. In a batch analysis, it is often the case that the user who has given an analysis-initiation command to the analyzing system leaves the system unattended and checks the analysis result after the completion of the analysis (e.g. next morning). The aforementioned operation by the analysis executer 93 prevents the reference liquid samples from being needlessly consumed.

As described to this point, the liquid sample introduction system for an ion source according to the present invention has the liquid-supply-gas passage 50 connected to a point in the nebulizer gas passage 41 connected to the ESI probe 30. A portion of the nebulizer gas is thereby introduced into the liquid sample containers 70a-70e, and the reference liquid samples in the liquid sample containers 70a-70e are sent to the ESI probe 30 by the pressure of this nebulizer gas.

Therefore, unlike the conventional system, it is unnecessary to provide a supply source of the liquid-supply gas for sending a liquid sample to the ESI probe, and the ionization of the liquid sample can be achieved at a low cost.

In the liquid sample introduction system for an ion source proposed in an international patent application (PCT/JP2015/077415) filed on the same date as the present application, when the nebulizer gas is supplied to the ion source, the atomization-promoting gas is also simultaneously supplied to the liquid sample containers as the liquid-supply gas. This causes the problem that the liquid sample is continuously supplied to the ionization probe and is needlessly consumed. By comparison, the liquid sample introduction system for an ion source according to the present embodiment can discontinue the supply of the liquid sample while continuing the supply of the nebulizer gas to the ion source. Therefore, the liquid sample will not be needlessly consumed.

In a TOF-MS, if the temperature of the device or its surroundings changes, or if the voltage applied to a specific section in the mass spectrometer varies, the relationship between the mass-to-charge ratio and time of flight of the ion will also change. Since an analysis with a TOF-MS needs to achieve a high mass accuracy on the order of ppm, it is common to introduce a reference liquid sample as the internal reference for mass calibration during the mass spectrometric analysis of a target liquid sample. With the liquid sample introduction system for an ion source according to the present embodiment, the operation of changing the kind of reference liquid sample or discontinuing the supply of the reference liquid sample can be performed while maintaining the continuous supply of the nebulizer gas to the ESI probe 30. Accordingly, no fluctuation in the pressure or gas flow within the ionization chamber 10 occurs, and the components eluted from the liquid chromatograph 80 can be ionized under stable conditions.

The liquid sample introduction system for an ion source according to the present embodiment uses nebulizer gas for the supply of liquid samples. Nebulizer gas is generally used for atmospheric pressure ionization of liquid samples, regardless of the kinds of liquid samples. Therefore, the present system can be used for a wide variety of liquid samples and ionization methods.

The liquid sample introduction system for an ion source according to the present embodiment uses a single six-position seven-way valve 61 to select one of the five liquid samples to be introduced into the ESI probe 30. Therefore, it is unnecessary to provide a number of passage-switching units as in a conventional liquid sample introduction system for an ion source (e.g. the one described in Patent Literature 1). This reduces the risk of the sample contamination at a passage-switching unit.

Additionally, in the liquid sample introduction system for an ion source according to the present embodiment, the regulator 51 located in the liquid-supply-gas passage 50 allows the pressure of the liquid-supply gas to be regulated independently of the pressure of the nebulizer gas so as to appropriately change the amount of liquid sample to be supplied.

The previous embodiment is a mere example and can be appropriately changed within the spirit of the present invention.

In the previous embodiment, five kinds of reference liquid samples are selectively introduced into the ESI probe. The liquids to be supplied to the ESI probe 30 are not limited to liquid samples for mass calibration. For example, target liquid samples may also be introduced. A liquid for cleaning the sample supply passage 60 as well as the sample-supply sub-passages 60a-60e may also be supplied. As another example, as shown in FIG. 4, the sub-port 61a may be connected to the exit port of the liquid chromatograph 80' so as to introduce a target liquid sample (or the various components in the same sample) from the liquid chromatograph 80' into the ESI probe through the six-position seven-way valve 61 and the sample supply passage 60. In this case, it is unnecessary to provide the ESI probe 20 for introducing a target liquid sample.

In place of the six-position seven-way valve 61 used as the passage-switching unit in the previous embodiment, a passage-switching unit having an appropriate number of sub-ports may be used according to the number of liquid samples to be supplied.

In place of the atmospheric open passage 62 in the previous embodiment, a passage for supplying an inert gas, such as nitrogen gas, may be connected to the sub-port 61f of the six-position seven-way valve 61. This configuration limits the kind of gas which is allowed to flow into the ionization chamber 10, which helps to keep the inside of the ionization chamber 10 clean. A closed-end passage may be connected to the sub-port 61f, in which case the supply of a liquid sample can be discontinued by connecting the sub-port 61f to the main port 61g.

Additionally, an APCI probe or other types of ionization probes may be used in place of the ESI probe 30 used as the ionization probe in the previous embodiment. In the case where an APCI probe is used, a drying gas can be used in place of the nebulizer gas in the previous embodiment. The drying gas is made to blow at the liquid sample from an opposite position to the tip of the APCI probe within the ionization chamber 10.

REFERENCE SIGNS LIST

10 . . . Ionization Chamber
11 . . . Capillary
20, 30 . . . ESI Probe
40 . . . Nitrogen Gas Cylinder (Atomization Gas Source)
41 . . . Nebulizer Gas Passage
42 . . . Valve
43, 52 . . . Branching Unit
50 . . . Liquid-Supply-Gas Passage
50a-50e . . . Liquid-Supply-Gas Sub-Passage
51 . . . Regulator
52 . . . Branching Unit
53 . . . Relief Valve
54 . . . Relief Passage
55 . . . Atmospheric Open Valve
56 . . . Atmospheric Open Passage
60 . . . Sample Supply Passage
60a-60e . . . Sample-Supply Sub-Passage
61 . . . Six-Position Seven-Way Valve
61a-61f . . . Sub-Port
61g . . . Main Port
62 . . . Atmospheric Open Passage
70a-70e . . . Liquid Sample Container
80, 80' . . . Liquid Chromatograph
90 . . . Control Unit
91 . . . Storage Section
92 . . . Analysis Condition Setter
93 . . . Analysis Executer
94 . . . Input Unit
95 . . . Display Unit

The invention claimed is:

1. A liquid sample introduction system for an ion source which ionizes a liquid sample by supplying the liquid sample to an ionization probe in an ion source and making an atomization-promoting gas blow at the liquid sample exiting from a tip of the ionization probe, the liquid sample introduction system comprising:
   a) a plurality of liquid sample containers, each of which is a hermetically closable container for holding a liquid sample;
   b) a liquid-supply-gas passage having one end connected to a point in a passage for an atomization-promoting gas leading to the ion source, and another end connected to a space above a liquid level in one of the liquid sample containers;
   c) a sample supply passage having one end connected to a space below the liquid level in one of the liquid sample containers and another end connected to the ionization probe; and
   d) a passage-switching unit, located in the sample supply passage, for switching the sample supply passage between a communicating state and a closed state,
where:
   the other end of the liquid-supply-gas passage is branched into a plurality of liquid-supply-gas sub-passages each of which is connected to the space above the liquid level in one of the liquid sample containers;
   the one end of the sample-supply passage is branched into a plurality of sample-supply sub-passages each of which is connected to the space below the liquid level in one of the liquid sample containers; and
   the passage-switching unit is a passage-switching valve placed at a branching point of the sample-supply sub-passages, the passage-switching valve having one main port and a plurality of sub-ports to be selectively connected to the main port, where one of the plurality of sub-ports is open to atmospheric pressure, and the plurality of sample-supply sub-passages are connected to the other sub-ports.

2. The liquid sample introduction system for an ion source according to claim 1, further comprising a liquid-supply-gas pressure regulator for regulating a pressure of the gas flowing through the liquid-supply-gas passage.

3. The liquid sample introduction system for an ion source according to claim 1, wherein one of the plurality of sub-ports is connected to an exit port of a liquid chromatograph.

4. An analyzing system, comprising:
   an ion analyzer for ionizing a target liquid sample after ionizing the liquid sample in an ionization chamber;
   the liquid sample introduction system for an ion source according to claim 1 for ionizing a reference liquid sample in the ionization chamber; and
   a processor configured to operate the liquid sample introduction system for an ion source so as to supply the reference liquid sample to the ionization probe during an execution of an analysis of an ion generated from the target liquid sample.

5. The analyzing system according to claim 4, wherein the processor is configured to operate the liquid sample introduction system to switch the passage-switching unit according to a kind of ion generated from the target liquid sample so as to change a kind of reference liquid sample to be supplied to the ionization probe or a presence or absence of a reference liquid sample to be supplied to the ionization probe.

6. The analyzing system according to claim 4, wherein the processor is configured to operate the passage-switching unit to switch the sample supply passage to the closed state if the reference sample is continuously supplied to the ionization probe continues for a predetermined length of time while no analysis is performed in the ion analyzer.

7. The analyzing system according to claim 4, wherein the ion analyzer includes a time-of-flight mass separator section.

8. The analyzing system according to claim 5, wherein the processor is configured to operate the passage-switching unit to switch the sample supply passage to the closed state if the reference sample is continuously supplied to the ionization probe continues for a predetermined length of time while no analysis is performed in the ion analyzer.

9. The analyzing system according to claim 5, wherein the ion analyzer includes a time-of-flight mass separator section.

* * * * *